United States Patent [19]
Watanabe et al.

[11] 4,357,470
[45] Nov. 2, 1982

[54] CEPHALOSPORIN COMPOUNDS

[75] Inventors: Yoshiaki Watanabe, Tokyo; Chihiro Yokoo, Saitama; Toshifumi Asaka, Saitama; Akira Onodera, Saitama; Kaoru Sota, Saitama; Jiro Sawada, Tokyo, all of Japan

[73] Assignee: Taisho Pharmaceutical Co., Ltd., Japan

[21] Appl. No.: 256,780

[22] Filed: Apr. 23, 1981

[30] Foreign Application Priority Data

May 10, 1980 [JP] Japan .................................. 55/61911

[51] Int. Cl.³ .......................................... C07D 501/56
[52] U.S. Cl. .......................................... 544/27; 544/28
[58] Field of Search .................................... 544/27, 28

[56] References Cited
U.S. PATENT DOCUMENTS

| 4,068,074 | 1/1978 | Murakami et al. | 544/27 |
| 4,156,724 | 5/1979 | Yamada et al. | 544/27 |
| 4,165,373 | 8/1979 | Yamada et al. | 544/27 |
| 4,190,581 | 2/1980 | Watanabe et al. | 260/239.1 |
| 4,217,450 | 8/1980 | Yasuda et al. | 544/27 |
| 4,223,037 | 9/1980 | Preiss et al. | 544/27 |
| 4,265,892 | 5/1981 | Kocsis et al. | 544/27 |
| 4,297,489 | 10/1981 | Gottstein et al. | 544/27 |

Primary Examiner—Paul M. Coughlan, Jr.
Attorney, Agent, or Firm—Wenderoth, Lind & Ponack

[57] ABSTRACT

Novel cephalosporin compounds having the general formula

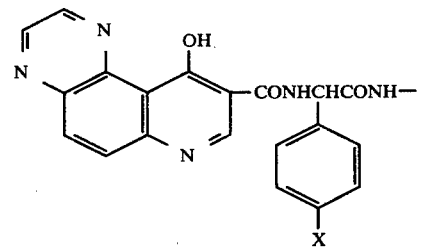

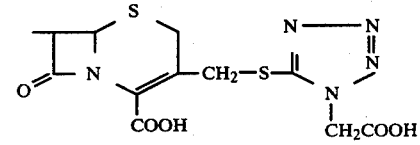

wherein X represents hydrogen atom or hydroxy group, and the non-toxic pharmacologically acceptable salts thereof are disclosed. These compounds are useful as antibacterial agents.

3 Claims, No Drawings

CEPHALOSPORIN COMPOUNDS

BACKGROUND OF THE INVENTION

A number of β-lactam antibiotics are known prior to the present invention, but nowhere are the antibiotics possessing any pyrazinoquinoline ring with the exception of penicillin compounds described in U.S. Pat. No. 4,190,581.

DESCRIPTION AND PREFERRED EMBODIMENT

The present invention relates to novel cephalosprin compounds having potent antibacterial activity. More particularly, it relates to a cephalosporin compound [hereinafter referred to as the compound (I)] having the general formula

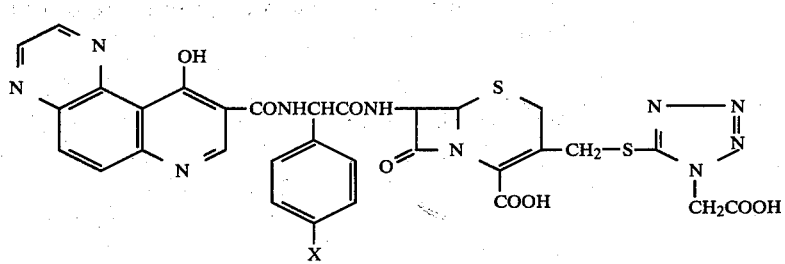

wherein X represents hydrogen atom or hydroxy group, and the salt thereof.

In the present invention, the salt of the compound (I) means a non-toxic pharmacologically acceptable salt such as an alkali metal salt, e.g., a sodium salt and a potassium salt; a salt with an organic base, e.g., a dicyclohexylamine salt, a cyclohexylamine salt, a trimethylamine salt, a triethylamine salt, an ethanolamine salt, an ornithine salt and a lysine salt; or an ammonium salt.

It is an object of the present invention to provide novel cephalosporin compounds which show potent antibacterial activities not only against Gram-positive bacteria but also against Gram-negative bacteria, especially, Pseudomonas species, indole-positive Proteus species, Klebsiella species, and the like and, moreover, show high blood levels for substantial period of time when applied.

According to the present invention, the compound (I) may be prepared, for example, by the following methods.

The compound [hereinafter referred to as the compound (II)] having the general formula

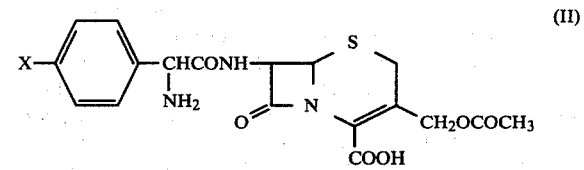

wherein X is as defined above, may be acylated with 4-hydroxy-pyrazino [2,3-f]quinoline-3-carboxylic acid [hereinafter referred to as the compound (III)], which may be prepared by the method described in British Patent Publication No. 2004877, to give the compound [hereinafter referred to as the compound (IV)] having the formula

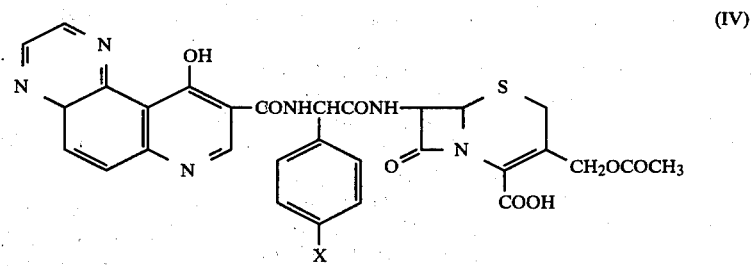

wherein X is as defined above. The acylation may be conducted by conventional methods.

The compound (IV) thus obtained or its salt may be reacted with 1-carboxymethyl-1H-tetrazole-5-thiol [hereinafter referred to as the compound (V)] to afford the compound (I). In the reaction of the compound (II) with the compound (III) to obtain the compound (IV), the compound (II), if necessary, may be used in the form of a salt or a derivative thereof wherein the carboxyl function has a protecting group. Suitable salts of the compound (II) include the salt with an inorganic acid (e.g., hydrochloric acid, sulfuric acid, phosphoric acid, or the like), an organic acid (e.g., acetic acid, trifluoroacetic acid, benzoic acid, or the like), an alkali metal (e.g., sodium, potassium, or the like), and an organic base (e.g., triethylamine, N,N-dimethylaniline, N-methylmorpholine, or the like). Examples of the protecting group of the compound (II) include benzhydryl, p-nitrobenzyl, 2,2,2-trichloroethyl and tertiary butyl groups. After completion of the reaction, the compound (IV) can be obtained by removing the protecting group of the reaction product by conventional methods. The compound (III), in this reaction, can be used in the form of a free acid, but desirably in the form of a reactive derivative such as the acid halide, the acid azide, the reactive ester, the acid anhydride or the reactive amide. Most preferred reactive derivatives of the compound (III) include the acid chloride, the acid azide, the ester constituted with p-nitrophenol or N-hydroxysuccinimide, the mixed acid anhydride with an alkylcarbonate and the mixed acid anhydride with an aliphatic carboxylic acid. In the present reaction, there may be employed a solvent such as water, chloroform, dichloromethane, tetrahydrofuran, dioxane, N,N-dimethylformamide, acetonitrile, ethylformate, ethyl acetate, dimethyl sulfoxide or hexamethylphosphoric triamide.

They may be used alone or mixed. If necessary, the reaction may be promoted by heating or addition of a reaction initiator.

The reaction of the compound (IV) with the compound (V) to obtain the compound (I) may be carried out at around neutral conditions in an inert solvent at room temperature or under heating. After completion of the reaction, the compound (I) thus prepared can be isolated by acidifying the reaction mixture or by extracting the reaction mixture with a suitable solvent to obtain the product. As the reaction solvent, there may be used a solvent such as water, acetone, N,N-dimethylformamide, dioxane, an alcohol or a phosphate buffer solution. These solvents may be used alone or mixed. In case where the compound (V) is used in the form of a free acid, the reaction may preferably be carried out in the presence of a base such as alkali hydroxide, alkali carbonate, alkali hydrogencarbonate, trialkylamine, pyridine, N,N-dimethylaniline or N-methylmorpholine.

Alternatively, the compound (I) may be prepared by reacting the compound [hereinafter referred to as the compound (VI)] having the general formula

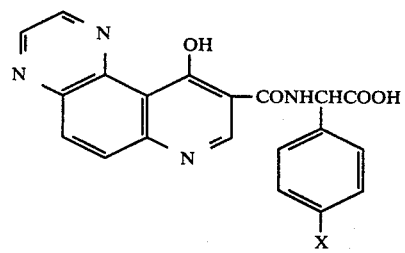

(VI)

wherein X is as defined above, with the compound [hereinafter referred to as the compound (VII)] having the general formula

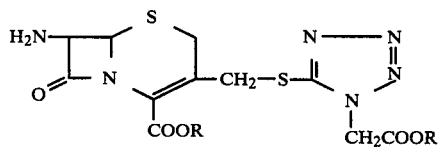

(VII)

wherein R represents hydrogen atom or a conventional protecting group. The reaction may be carried out by conventional methods. It is desirable to use the compound (VI) in the form of a reactive derivative such as the acid halide, the acid azide, the reactive ester, the acid anhydride or the reactive amide. Especially it gives a good result to employ the acid chloride, the acid azide, the ester with p-nitrophenol or N-hydroxysuccinimide, the mixed acid anhydride with an alkylcarbonate, the mixed acid anhydride with an aliphatic carboxylic acid, and the like. The compound (VII) may be used in the form of a free acid, but, if necessary, it may be used in the form of a salt. The conventional protecting group of R of the compound (VII) includes benzhydryl, p-nitrobenzyl, 2,2,2-trichloroethyl and tertiary butyl groups, and the like. Suitable salts of the compound (VII) include the salt constituted with an inorganic acid (e.g., hydrochloric acid, sulfuric acid, phosphoric acid, or the like), an organic acid (e.g., acetic acid, trifluoroacetic acid, benzoic acid, or the like) and an organic base (e.g., triethylamine, N,N-dimethylaniline, N-methylmorpholine, or the like). The reaction may be carried out in a solvent such as water, chloroform, dichloromethane, tetrahydrofuran, dioxane, N,N-dimethylformamide, dimethyl sulfoxide, hexamethylphosphoric triamide, acetonitrile, ethyl formate, ethyl acetate, or the like. These solvents may be used alone or mixed. The reaction, if necessary, may be promoted by heating or addition of an initiator.

The compound (VI) may be obtained by condensing a D-α-phenylglycine compound having the general formula

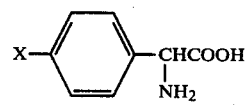

wherein X is as defined above, with the compound (III). In the condensation, the compound (III) may be employed in the form of a free acid or a reactive derivative described above.

As a further alternative, the compound (I) may be obtained by acylating the compound [hereinafter referred to as the compound (VIII)] having the general formula

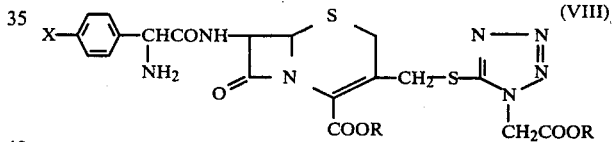

(VIII)

wherein R and X are defined above, which is prepared according to the method described in German Patent Laid-Open No. 2,538,804 with the compound (III). The acylation may be carried out by conventional manners. The compound (III) may be employed in the form of a free acid or a reactive derivative described above. The compound (VIII) may be employed in the form of a free acid, but, if necessary, it may be used in the form of a salt. The conventional protecting groups of the compound (VIII) include benzhydryl, p-nitrobenzyl, 2,2,2-trichloroethyl, and tertiary buty groups, and the like. Suitable salts of the compound (VIII) are the salt constituted with an inorganic acid (e.g., hydrochloric acid, sulfuric acid, phosphoric acid, or the like), an organic acid (e.g., acetic acid, trifluoroacetic acid, benzoic acid, or the like), an alkali metal (e.g., sodium, potassium, or the like) and an organic base (e.g., triethylamine, N,N-dimethylaniline, N-methylmorpholine, or the like). In the case where group R of the compound (VIII) is a conventional protecting group, the group R, after completion of the acylation, may be removed from the reaction product by conventional methods to give the compound (I). The reaction may be carried out in a solvent such as water, chloroform, dichloromethane, tetrahydrofuran, dioxane, N,N-dimethylformamide, dimethyl sulfoxide, hexamethylphosphoric triamide, acetonitrile, ethyl formate, ethyl acetate, or the like. These solvents may be used alone or mixed. The reaction, if necessary, may be promoted by heating or addition of an initiator.

The pharmaceutical acceptable salts of the compound (I) described above may be obtained by treating the compound (I) with the corresponding base in the conventional manners.

As stated above, the compounds of the present invention have high anti-bacterial activities against Gram-positive and Gram-negative bacteria, and show high blood levels for substantial period of time. Accordingly, they may be used as antibacterial agents in the same manner as other cephalosporin compounds. For example, they may be used in mammals in an amount of 1 mg to 100 mg/kg, daily, parenterally, in single or two to four divided doses to treat bacterial infections, e.g., 10 mg/kg in mice.

The compounds of the present invention are of low toxicity. For example, 7-[D-α-(4-hydroxy-pyrazino[2,3-f]-quinoline-3-carboxamido)-α-(4-hydroxyphenyl)acetamido]-3-(1-carboxymethyl-tetrazole-5-yl)thiomethyl-Δ³-cephem-4-carboxylic acid disodium salt hardly shows any intraperitoneal acute toxicity in rats at a dose less than 5000 mg/kg of body weight.

The compounds of the present invention may be used alone or in combination as the active ingredients in any one or a variety of pharmaceutical preparations. They may be administered by parenteral injections such as subcutaneous, intramuscular or intravenous injection, in the form of solution or suspension in suitable media, e.g., sterile water, saline, glycols, oils, or as dry preparations suitable for the extempore preparation of injectable forms. In addition, the compounds of the present invention may be administered in the form of a suppository in suitable media, e.g., stearic acid, its salt, talc, vegitable oils and gycols.

The following Experiments are given in order to prove that the compounds of the present invention have potent antibacterial activities against various bacteria and give a prolonged high blood levels.

Experiment 1

Antibacterial activities of the compounds of the present invention were tested about various microorganisms using an agar plate dilution method. Commercial cefazolin sodium was used as a control. The test results for 7-[D-α-(4-hydroxy-pyrazino[2,3-f]quinoline-3-carboxamido)-α-phenylacetamido]-3-(1-carboxymethyl-tetrazole-5-yl)thiomethyl-Δ³-cephem-4-carboxylic acid disodium salt (TC-203) and 7-[D-Δ-(4-hydroxy-pyrazino[2,3-f]quinoline-3-carboxamido)-Δ-(4-hydroxyphenyl)acetamido]-3-(1-carboxymethyl-tetrazole-5-yl)thiomethyl-Δ³-cephem-4-carboxylic acid disodium salt (TC-403) are expressed by MIC value (Minimum Inhibitory Concentration, μg/ml) and shown in Table 1.

TABLE 1

| | MIC (μg/ml) | | |
|---|---|---|---|
| | compound | | |
| Microorganism | TC-203 | TC-403 | cefazolin sodium |
| Staphylococcus aureus FDA 209 P | 3.13 | 6.25 | <0.1 |
| Escherichia coli NIHJC-2 | 0.78 | 1.56 | 1.56 |
| Klebsiella pneumoniae 3K-2 | 0.78 | 1.56 | >100 |
| Pseudomonas aeruginosa NC-5 | 12.5 | 12.5 | >100 |
| Proteus vulgaris IID 874 | 1.56 | 3.13 | >100 |

Experiment 2

The compounds of the present invention were administered to mice intramuscularly and change of blood levels with lapse of time was determined. Commercial cefazolin sodium was used as a control. The results are shown in Table 2.

TABLE 2

| | Blood levels (μg/ml) | | | |
|---|---|---|---|---|
| | Time after administration (minutes) | | | |
| Compounds | 15 | 30 | 60 | 120 |
| TC-203 | 150 | 162 | 82 | 32 |
| TC-403 | 92 | 180 | 62 | 42 |
| cefazolin sodium | 62 | 42 | 5.5 | — |

Note: TC-203 and TC-403 in the compound column are as defined with reference to Experiment 1.

The present invention is illustrated by the following examples.

EXAMPLE 1

(1) In a mixture of 10 ml of dimethysulfoxide and 3 ml of dichloromethane were suspended 441 mg of cephaloglycine dihydrate and 338 mg of 4-hydroxy-pyrazino[2,3-f]quinoline-9-carboxylic acid N-hydroxysuccinimide ester. To the suspension was added 0.14 mg of trimethylamine, followed by stirring for 3 hours under ice cooling. To this was added 0.8 ml of 30% solution of sodium 2-ethylhexanoate in n-butanol and the mixture was stirred for 15 minutes. After addition of 100 ml of ethyl acetate, the precipitated crystals were collected, washed with ethyl acetate and dried to give 450 mg of 7-[D-α-(4-hydroxy-pyrazino[2,3-f]quinoline-3-carboxamide)-α-phenylacetamido]cephalosporanic acid sodium salt.

m.p. 280° C. (decomposition)

IR$\nu_{max}^{KBr}$=1770 cm$^{-1}$ (β-lactam)

NMR (DMSO-d$_6$)

δ=1.58 (3H, s), 3.40 (2H, broad s), 4.80 (2H, broad s), 5.15 (1H, d, J=5 Hz), 5.80–6.20 (1H, m), 6.75 (1H, d, J=7 Hz), 7.10–7.70 (5H, m), 8.21 (1H, d, J=10 Hz), 8.46 (1H, d, J=10 Hz), 8.76 (1H, s), 9.12 (1H, d, J=2 Hz), 9.29 (1H, d, J=2 Hz), 11.98 (1H, d, J=7 Hz).

(2) 2.5 g of 7-[D-α(4-hydroxy-pyrazino[2,3-f]quinoline-3-carboxamido)-α-phenylacetamido]cephalosporanic acid sodium salt obtained by the method of the step (1) described above were dissolved in 10 ml of ice water, and adjusted to pH 2 by 10% hydrochloric acid. The precipitated crystals were collected and dried to give 2.1 g of 7-[D-α-(4-hydroxy-pyrazino[2,3,-f]quinoline-3-carboxamido)-α-phenylacetamido]cephalosporanic acid. In 90 ml of water were suspended 1.89 g of 7-[D-α-(4-hydroxy-pyrazino[2,3-f]quinoline-3-carboxamido)-α-phenylacetamido[cephalosporanic acid, 628 mg of 1-carboxymethyltetrazole-5-thiol and 882 mg of sodium hydrogencarbonate. The resulting suspension was stirred for 13 hours at 50°–60° C. The mixture was diluted with 300 ml of ice water and adjusted to pH 2 by addition of 10% hydrochloric acid. The precipitated crystals were collected, washed with acetone and dried. The resulting crystals were suspended to 50 ml of methylene chloride. 0.55 ml of triethylamine was added to the above suspension to dissolve the crystals. Insolubles were filtered off. To the resulting filtrate was added 2 ml of a 30% solution of sodium 2-ethylhexanoate in n-butanol. The precipitated crystals were collected and dried to afford 448 mg of 7-[D-α-(4-hydroxy-pyrazino[2,3-f]quinoline-3-carboxamido)-α-phenylacetamido]-3-(1-carboxymethyl-tetrazole-5-yl)thiomethyl-Δ³-cephem-4-carboxylic acid disodium salt.

m.p. 275°–278° C. (with decomposition)

IR$\nu_{max}^{KBr}$=1760 cm$^{-1}$ (β-lactam)

NMR (DMSO-d$_6$-D$_2$O)

δ=3.51 (2H, broad s), 4.32 (2H, broad s), 4.67 (2H, broad s), 5.03 (1H, d, J=5 Hz), 5.79 (1H, d, J=5 Hz), 6.27 (1H, s), 7.20–7.82 (5H, m), 8.29 (2H, s), 8.88 (1H, s), 9.06 (1H, d, J=2 Hz), 9.23 (1H, d, J=2 Hz).

EXAMPLE 2

(1) In a mixture of 10 ml of a 10% aqueous sodium hydroxide solution, 40 ml of water and 40 ml of pyridine was dissolved 3.02 g of D-α-phenylglycine at room temperature. 6.76 g of 4-hydroxy-pyrazino[2,3-f]quinoline-3-carboxylic acid N-hydroxysuccinimide ester was added to the above solution, followed by stirring for 2 hours. After completion of the reaction, insolubles were filtered off and the filtrate was adjusted to pH 3 by addition of 10% hydrochloric acid. Precipitated yellow crystals were collected, washed with acetone and dried in vacuo to give 7.20 g of D-α-(4-hydroxy-pyrazino[2,3-f]quinoline-3-carboxamido) phenylacetic acid. The product thus obtained was employed as the starting material in the next step (2) for preparing the desired compound of the present invention.

m.p. 280°–283° C. (with decomposition)

IR$\nu_{max}^{Nujol}$=1708 cm$^{-1}$ (—COOH), 1655 cm$^{-1}$ (—CONH—)

NMR (DMSO-d$_6$)

δ=5.57 (1H, d, J=7 Hz), 7.38 (5H, s), 7.96 (2H, d, J=9 Hz), 8.17 (2H, d, J=9 Hz), 8.69 (1H, s), 8.87 (1H, d, J=2 Hz), 9.00 (1H, d, J=2 Hz), 11.10 (1H, d, J=7 Hz).

(2) In 5 ml of ethyl acetate was suspended 372 mg of 7-amino-3-(1-carboxymethyl-tetrazole-5-yl)thiomethyl-Δ³-cephem-4-carboxylic acid. To the suspension was added 1 ml of N,O-bistrimethysilylacetamide, followed by stirring at room temperature for 30 minutes to give a solution.

On the other hand, 374 mg of D-α-(4-hydroxy-pyrazino[2,3-f]quinoline-3-carboxamido)phenylacetic acid, which had been obtained in the above step (1), was dissolved in a mixture of 10 ml of N,N-dimethylformamide and 0.11 ml of N-methylmorpholine. The solution was cooled to −60° C. and then 0.13 ml of isobutyl chlorocarbonate was added thereto. The mixture was maintained at that temperature for 20 minutes. To the reaction mixture was added the solution obtained in the above procedure over about 5 minutes. The resulting mixture was stirred at −40°–−35° C. for 6 hours. After completion of the reaction, the mixture was diluted with 50 ml of ice water, adjusted to pH 2 with 10% hydrochloric acid and extracted with ethyl acetate. The extract was washed with water and dried over mangesium sulfate, and the ethyl acetate was distilled off. The resulting residue was dissolved in a mixture of 5 ml of dimethylsulfoxide and 0.14 ml of triethylamine. After addition of 0.5 ml of a 30% solution of sodium 2-ethylhexanoate in n-butanol, the solution was stirred for 15 minutes. To the resulting solution was added 50 ml of ethyl acetate. Precipitated crystals were collected and dried to afford 316 mg of 7-[D-α-(4-hydroxy-pyrazino[2,3-f]quinoline-3-carboxamido)-α-phenylacetamido]-3-(1-carboxymethyl-tetrazole-5-yl)thiomethyl-Δ³-cephem-4-carboxylic acid disodium salt. Physical properties of this compound were identified with those of the compound obtained in Example 1.

EXAMPLE 3

In a mixture of 10 ml of dimethylsulfoxide and 3 ml of dichloromethane were suspended 557 mg of 7-(D-α-amino-α-phenylacetamido)-3-(1-carboxymethyl-tetrazole-5-yl)thiomethyl-Δ³-cephem-4-carboxylic acid·trifluoroacetic acid salt and 304 mg of 4-hydroxy-pyrazino[2,3-f]quinoline-3-carboxylic acid N-hydroxysuccinimide ester. To the suspension was added 0.5 ml of triethylamine under ice-cooling and the mixture was stirred at that temperature for 4 hours. Then 1 ml of a 30% solution of sodium 2-ethylhexanoate in n-butanol was added to the above mixture, followed by stirring for 15 minutes. 100 ml of ethyl acetate was added to the mixture. Precipitated crystals were collected, washed with ethyl acetate and dried in vacuo to obtain 580 mg of 7-[D-α-(4-hydroxy-pyrazino[2,3-f]quinoline-3-carboxamido)-α-phenylacetamido]-3-(1-carboxymethyl-tetrazole-5-yl)thiomethyl-Δ³-cephem-4-carboxylic acid disodium salt. Physical properties of the compound were identified with those of the compound obtained in Example 1.

EXAMPLE 4

In a mixture of 8 ml of dimethylsulfoxide and 3 ml of dichloromethane were suspended 320 mg of 7-[D-α-amino-α-(4-hydroxyphenyl)acetamido]-3-(1-carboxymethyl-tetrazole-5-yl)thiomethyl-Δ³-cephem-4-carboxylic acid·trifluoroacetic acid salt and 169 mg of 4-hydroxy-pyrazino[2,3-f]quinoline-3-carboxylic acid N-hydroxysuccinimide ester. To the resulting suspension was added 0.3 ml of triethylamine under ice-cooling, followed by stirring at that temperature for 3 hours. Then 1 ml of a 30% solution of sodium 2-ethylhexanoate in n-butanol was added to the above mixture, followed by stirring for 30 minutes. 100 ml of ethyl acetate was added to the mixture. Precipitated crystals were collected, washed with ethyl acetate and dried in vacuo to afford 310 mg of 7-[D-α-(4-hydroxy-pyrazino[2,3-f]quinoline-3-carboxamide)-α-(4-hydroxyphenyl)acetamido]-3-(1-carboxymethyl-tetrazole-5-yl)thiomethyl-Δ³-cephem-4-carboxylic acid disodium salt.

m.p. 253° C. (with decomposition)

IR$\nu_{max}^{KBr}$=1762 cm$^{-1}$ (β-lactam)

NMR (DMSO-d$_6$-D$_2$O)

δ=3.48 (2H, broad s), 4.29 (2H, broad s), 4.68 (2H, broad s), 4.93 (1H, d, J=5 Hz), 5.67 (1H, d, J=5 Hz), 5.93 (1H, s), 6.78 (2H, d, J=8 Hz), 7.42 (2H, d, J=8 Hz), 8.08 (2H, s), 8.93 (1H, d, J=2 Hz), 9.01 (1H, s), 9.12 (1H, d, J=2 Hz).

What is claimed is:

1. Cephalosporin compound having the general formula

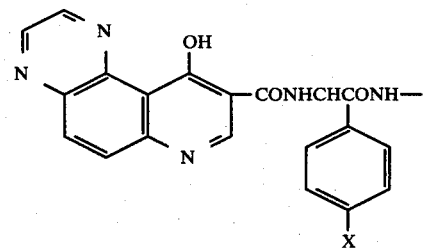

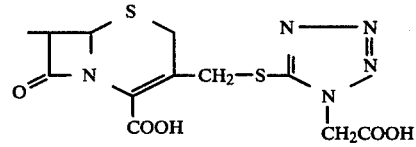

wherein X represents a hydrogen atom or hydroxy group, and the non-toxic pharmacologically acceptable salts thereof.

2. A compound according to claim 1 is 7-[D-α-(4-hydroxy-pyrazino[2,3-f]quinoline-3-carboxamido)-α-phenylacetamido]-3-(1-carboxymethyl-tetrazole-5-yl)thiomethyl-Δ³-cephem-4-carboxylic acid and non-toxic pharmacologically acceptable salts thereof.

3. A compound according to claim 1 is 7-[D-α-(4-hydroxy-pyrazino[2,3-f]quinoline-3-carboxamido)-α-(4-hydroxyphenyl)acetamido]-3-(1-carboxymethyl-tetrazole-5-yl)thiomethyl-Δ³-cephem-4-carboxylic acid and non-toxic pharmacologically acceptable salts thereof.

* * * * *